United States Patent
Hadley et al.

(10) Patent No.: US 10,459,211 B2
(45) Date of Patent: Oct. 29, 2019

(54) RESONANT SCANNER INTEROPERATION WITH MOVABLE STAGE

(71) Applicant: CALIBER IMAGING & DIAGNOSTICS, INC., Rochester, NY (US)

(72) Inventors: Keith Aaron Hadley, Rochester, NY (US); Jason William Faulring, Livonia, NY (US); Paul Michael Hemmer, Rochester, NY (US); James Vincent Massaro, Rochester, NY (US)

(73) Assignee: Caliber Imaging & Diagnostics, Inc., Rochester, NY (US)

(*) Notice: Subject to any disclaimer, the term of this patent is extended or adjusted under 35 U.S.C. 154(b) by 197 days.

(21) Appl. No.: 15/730,668

(22) Filed: Oct. 11, 2017

(65) Prior Publication Data
US 2018/0129031 A1    May 10, 2018

Related U.S. Application Data

(60) Provisional application No. 62/406,841, filed on Oct. 11, 2016.

(51) Int. Cl.
*G02B 26/08* (2006.01)
*G02B 21/26* (2006.01)
*G01N 33/483* (2006.01)
*G02B 21/00* (2006.01)

(52) U.S. Cl.
CPC ......... *G02B 21/26* (2013.01); *G01N 33/4833* (2013.01); *G02B 21/008* (2013.01); *G02B 21/0028* (2013.01); *G02B 21/0032* (2013.01); *G02B 21/0048* (2013.01)

(58) Field of Classification Search
CPC ............... G02B 21/26; G02B 21/0028; G02B 21/0032; G02B 21/0048; G02B 21/008; G01N 33/4833
USPC ...................................................... 359/213.1
See application file for complete search history.

(56) References Cited

U.S. PATENT DOCUMENTS

| | | |
|---|---|---|
| 5,788,639 A | 8/1998 | Zavislan et al. |
| 5,880,880 A | 3/1999 | Anderson et al. |
| 6,429,968 B1 | 8/2002 | Carver |
| 7,394,592 B2 | 7/2008 | Fox et al. |
| 9,055,867 B2 | 6/2015 | Fox et al. |
| 9,339,178 B2 * | 5/2016 | Yu .................... A61B 3/0008 |
| 9,952,205 B2 | 4/2018 | Abeytunge et al. |
| 2003/0206341 A1 | 11/2003 | Wolleschensky et al. |
| 2004/0119004 A1 | 6/2004 | Wine et al. |

(Continued)

OTHER PUBLICATIONS

Abeytunge, S. et al., Rapid confocal imaging of large areas of excised tissue with strip mosaicing, Journal of Biomedical Optics, vol. 16(5), May 2011.

(Continued)

*Primary Examiner* — Euncha P Cherry
(74) *Attorney, Agent, or Firm* — Kenneth J. Luckacher Law Group; R. Stephen Rosenholm

(57) ABSTRACT

A system, apparatus and method and method for controlling interoperation between a resonant scanner and a movable stage. The movable stage being employed to position a specimen for optical scanning by the resonant scanner. The invention providing high resolution scanning of specimen tissue at a rate of ten times or more faster than other known methods of optically scanning a specimen.

21 Claims, 7 Drawing Sheets

(56) References Cited

U.S. PATENT DOCUMENTS

2004/0133112 A1     7/2004   Rajadhyaksha
2015/0173606 A1     6/2015   Yu et al.
2015/0351633 A1   12/2015   Fox et al.

OTHER PUBLICATIONS

Abeytunge, S. et al., Confocal microscopy with strip mosaicing for rapid imaging over large areas of excised tissue, Journal of Biomedical Optics, vol. 18(6), Jun. 2013.

* cited by examiner

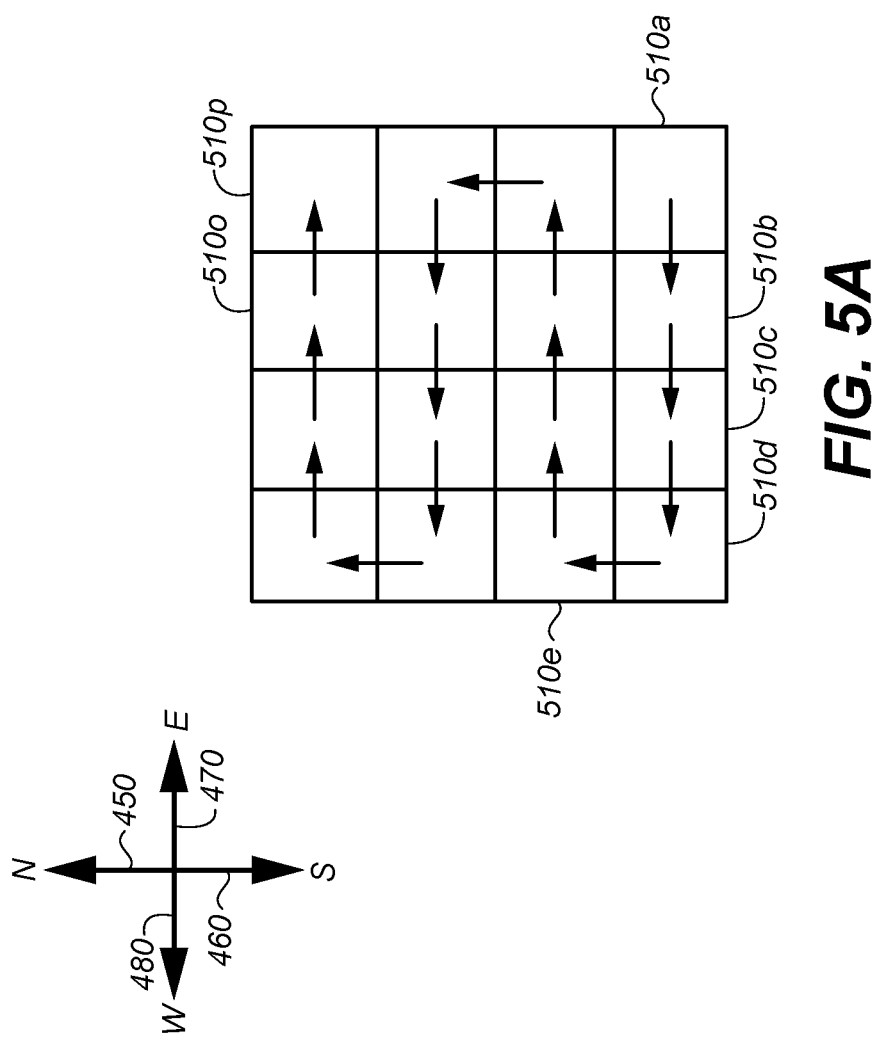

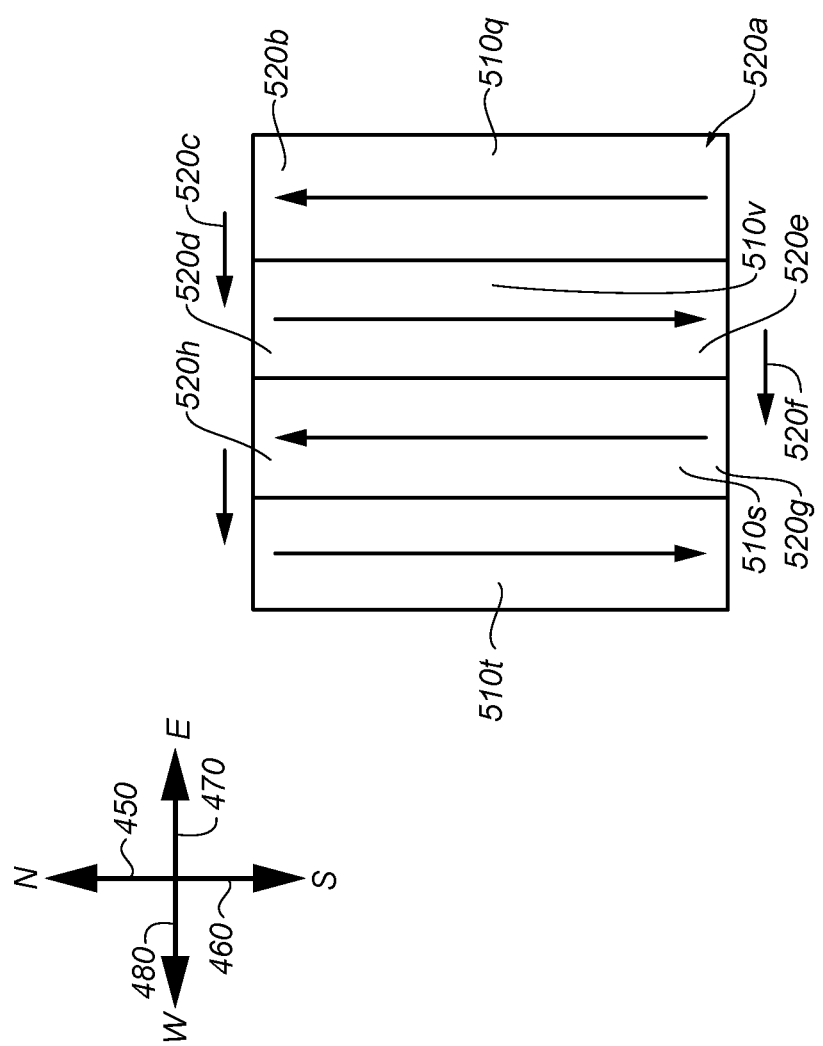

RESONANT SCANNER INTEROPERATION WITH MOVABLE STAGE

CROSS REFERENCE TO RELATED PATENT APPLICATION(S)

The document is a United States non-provisional utility patent application that claims priority and benefit to co-pending U.S. (utility) provisional patent application having Ser. No. (62/406,841), (Confirmation No. 3165), that was filed on Oct. 11, 2016, and that is entitled "CONTROLLING INTER-OPERATION BETWEEN A RESONANT SCANNER AND A MOVABLE STAGE", and which is incorporated herein by reference in its entirety.

PATENT APPLICATION(S) INCLUDING RELATED SUBJECT MATTER

This document is a United States non-provisional utility patent application, that includes subject matter generally related to that of U.S. Pat. No. 9,055,867 to Fox et al., that was issued on Jun. 16, 2015 and entitled "CONFOCAL SCANNING MICROSCOPE HAVING OPTICAL AND SCANNING SYSTEMS WHICH PROVIDE A HAND-HELD IMAGING HEAD".

This document includes subject matter that is also generally related to that of U.S. Patent Publication No. 2015/0351633 which was published on Dec. 10, 2015 and that was filed as a continuation patent application related to the prior filed U.S. patent application Ser. No. 11/920,195, which later issued as the U.S. Pat. No. 9,055,867 referred to above. The aforementioned patents, patent publications and patent applications are incorporated herein by reference in their entirety.

FIELD OF THE INVENTION

An apparatus for controlling interoperation between a resonant scanner and a movable stage. The movable stage being employed to position a specimen for optical scanning by the resonant scanner.

BACKGROUND OF THE INVENTION

A resonant scanner employs a resonating mirror that deflects and directs a beam of light. A position of the resonating mirror is dynamic over time, and meaning that the mirror is designed to resonate (oscillate) over time in accordance with a particular oscillating frequency. Such resonating causes a direction of the beam of light to also oscillate and change over time.

The discussion above is merely provided for general background information and is not intended to be used as an aid in determining the scope of the claimed subject matter.

BRIEF DESCRIPTION OF THE INVENTION

An apparatus, system and method or controlling interoperation between a resonant scanner and a movable stage. The movable stage being employed to position a specimen for optical scanning by the resonant scanner. The invention providing high resolution scanning of specimen tissue at a rate exceeding a factor of ten times faster than other known methods of optically scanning a specimen.

This brief description of the invention is intended only to provide a brief overview of subject matter disclosed herein. This brief description is not intended to identify key features or essential features of the claimed subject matter, nor is it intended to be used as an aid in determining the scope of the claimed subject matter.

BRIEF DESCRIPTION OF THE DRAWINGS

So that the manner in which the features of the invention can be understood, a detailed description of the invention may be had by reference to certain embodiments, some of which are illustrated in the accompanying drawings. The drawings are not necessarily to scale, and the emphasis generally being placed upon illustrating the features of certain embodiments of the invention. In the drawings, like numerals are used to indicate like parts throughout the various views. For further understanding of the invention, reference can be made to the following detailed description, read in connection with the drawings in which:

FIG. 5A-5B illustrate a path of stage movement for step-mapping and strip-mapping.

DETAILED DESCRIPTION OF THE INVENTION

Figure 1:
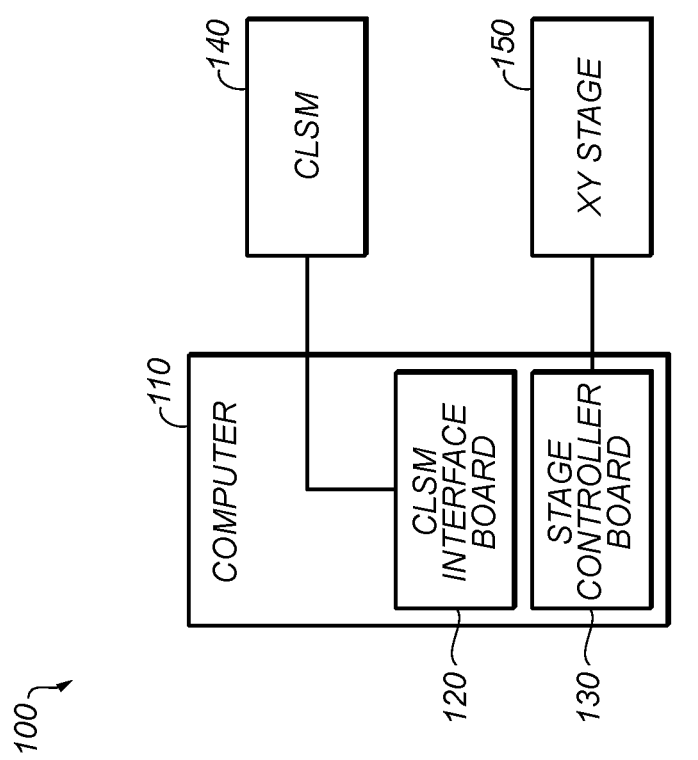
FIG. 1 illustrates a block diagram of an embodiment of an electrical interface between a confocal laser scanning microscope (CLSM) and a movable stage.

FIG. 1 illustrates a block diagram 100 of a system, apparatus and method of an embodiment of electrical interface between a confocal laser scanning microscope (CLSM) 140 and a movable XY stage 150, also referred to herein as a stage 150. As shown, a computer 110 including expansion slots and various (hardware) components that electrically interface with other parts of the computer via a system bus. The hardware components, and software stored within memory and the system bus being located within the computer chassis (not shown here).

A confocal laser scanning microscope (CLSM) interface board 120 is a component that is designed to electrically interface with a confocal laser scanning microscope (CLSM) 140. A stage controller board 130 is a component that is designed to electrically interface with stage 150. The XY stage 150 is designed to move within the confines of a two dimensional XY plane, defined by the X and Y axes, while physically contacting and supporting a specimen from gravity. The specimen is typically a portion of tissue including cellular structures within it. However, a specimen is not limited to being composed of living and/or prior living material, and can be partially or entirely composed of non-living and/or never living material. A mechanical stand (not shown) is employed to position the CLSM 140 and to support the CLSM 140 from gravity as it is disposed above and directed towards the stage 150.

The two dimensional XY plane, also referred to herein as a XY plane, is defined by two orthogonal directions referred to herein as the X axis and the Y axis (See FIG. 2), which are also referred to herein as the X direction and the Y direction, respectively. This plane is oriented substantially parallel to the surface of the earth, and being substantially perpendicular to the direction of gravity. As referred to herein, a Z axis, which is also referred to herein as a Z direction, is defined to be substantially parallel to the direction of gravity and perpendicular to the two dimensional XY plane.

In some embodiments, a Marzhauser Scan Plus 1M 120× 80—part number 00-24-579-0000 is employed as an XY stage, and a Marzhauser Tango PCIe Stage Controller—part number 00-76-150-0812, is employed as a stage controller. The stage is moved by stepper motors that are controlled by the Marzhauser Tango PCIe Stage Controller. In other embodiments, the stage is ProScan motorized stage manufactured by Prior Scientific, for example, part number H101CNLI.

The confocal laser scanning microscope (CLSM) 140 is designed to provide images generated from an optical scan via a focused point illumination (laser) towards a two-dimensional plane, within a specimen. The two-dimensional plane coincides with a location of a thin layer of tissue that is intended to be optically scanned within the specimen. This this layer of tissue can be as thin as a micron or less in thickness.

A light-sensitive detector is employed in combination with a pin hole that is located in the optically conjugate focal plane. The optically conjugate focal plane is disposed at a location in space in accordance with a location of the two-dimensional plane and the layer to be optically scanned within the specimen.

Figure 2:
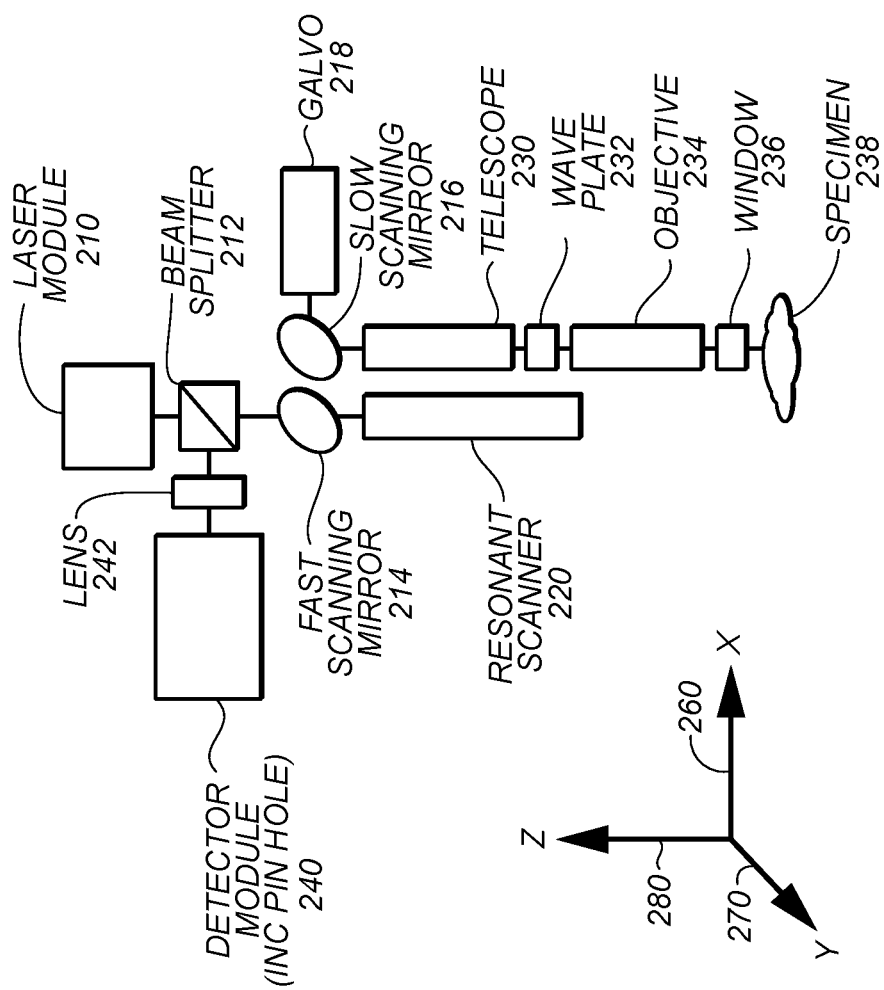
FIG. 2 illustrates a block diagram of some of the internal components within an embodiment of a confocal laser scanning microscope (CLSM).

FIG. 2 illustrates a block diagram 200 of some of the internal components of an embodiment of a confocal laser scanning microscope (CLSM) 140. As shown, the CLSM 140 includes a laser module 210, beam splitter 212, fast scanning mirror 214, slow scanning mirror 216 and galvanometer 218. The laser module generates a laser beam (not shown) that passes through the beam splitter 212 and on the return path it is reflected by the beam splitter towards the detector.

A first of these two beams first reflects off of the fast scanning mirror 214 then reflects off of the slow scanning mirror 216 in route to being directed towards a specimen 238. Prior to arriving at the specimen 238, the laser beam passes through a telescope 230, a wave plate 232, an objective lens 234 and a window 236 portion of the CLSM 140.

The window 236 is made from a ridged and translucent material. Such material is attached to the scan head and/or attached to a slide holding the specimen 238 itself. An index matching fluid is disposed adjacent to the window 236 for the purpose of optical refractive index matching. Such fluid can be an oil, gel, water or in some circumstances, air.

The fast scanning mirror 214 oscillates horizontally between two extreme positions and along a direction that is substantially parallel to the X axis 260, while the slow scanning mirror 216 moves along a direction that is substantially parallel to the Y axis. Via the oscillation of the fast scanning mirror 214 between two extreme positions, a direction of the laser bean oscillates between two extreme directions.

A galvanometer 218 is employed to control the movement of the slow scanning mirror 216. The galvanometer 218 is also referred to herein as a "galvo", and is an electromechanical instrument that is designed to move precisely in response to receiving an electrical signal. The CLSM 140 further includes a resonant scanner 220 component which is employed to cause oscillating movement of the fast scanning mirror 214.

The CLSM 140 further includes a telescope 230, which is designed to pass light and which includes one or more lenses (not shown). The CLSM 140 further includes a wave plate 232 and objective lens 234 and a window 236. The window 236 passes light towards the specimen 238 and receives light that is reflected off of a specimen 238 and back into the CLSM 140.

Light reflecting off the specimen 238 passes through the window 236, the objective lens 234, the wave plate 232, the telescope 230, and is reflected by the beam splitter 212 through a detector module input lens 242 into a detector module 240. The detector module 240 is designed to process light that is received through a light input aperture, which is also referred to herein as a "pine hole".

The pin hole of the detector module 242 is positioned to receive light that is reflected off a scanning plane that is located within the specimen 238. Such light that is reflected off a scanning plane, referred to here as reflected light, is captured along an optical focal plane, having a particular location in three dimensional space, and that is associated with that particular scanning plane within the specimen 238.

Typically, an internal portion of the specimen 238 is optically scanned along a scanning plane that is located at particular depth (distance) within the specimen, as measured from an outer surface of the specimen 238 that is nearest to the CLSM 140. This outer surface is typically a highest elevated (upper) surface of the specimen, considering that the CLSM 140 is typically disposed at a higher elevation above the specimen 238.

A plurality of scanning planes are located within a three dimensional space that is occupied by the specimen 238. Each of a plurality of scanning planes is oriented perpendicular to the Z direction and layered (stacked) together along the Z direction within the specimen 238. Each of these scanning plates is associated with a particular focal plan. The detector module 242 is designed to input light reflected from each scanning plane. Via the detector module, a three dimensional image of at least a portion of the specimen 238, or optionally of the entire specimen, is stored into a memory as digital data.

In accordance with some embodiments of the invention, a version of the CLSM 140 of FIG. 2 is employed where in certain mode of operation, movement of the slow mirror scanning mirror 216 is substituted for by a moving XY stage, while the fast scanning mirror 214 continues to move in an oscillating fashion.

Figure 3:
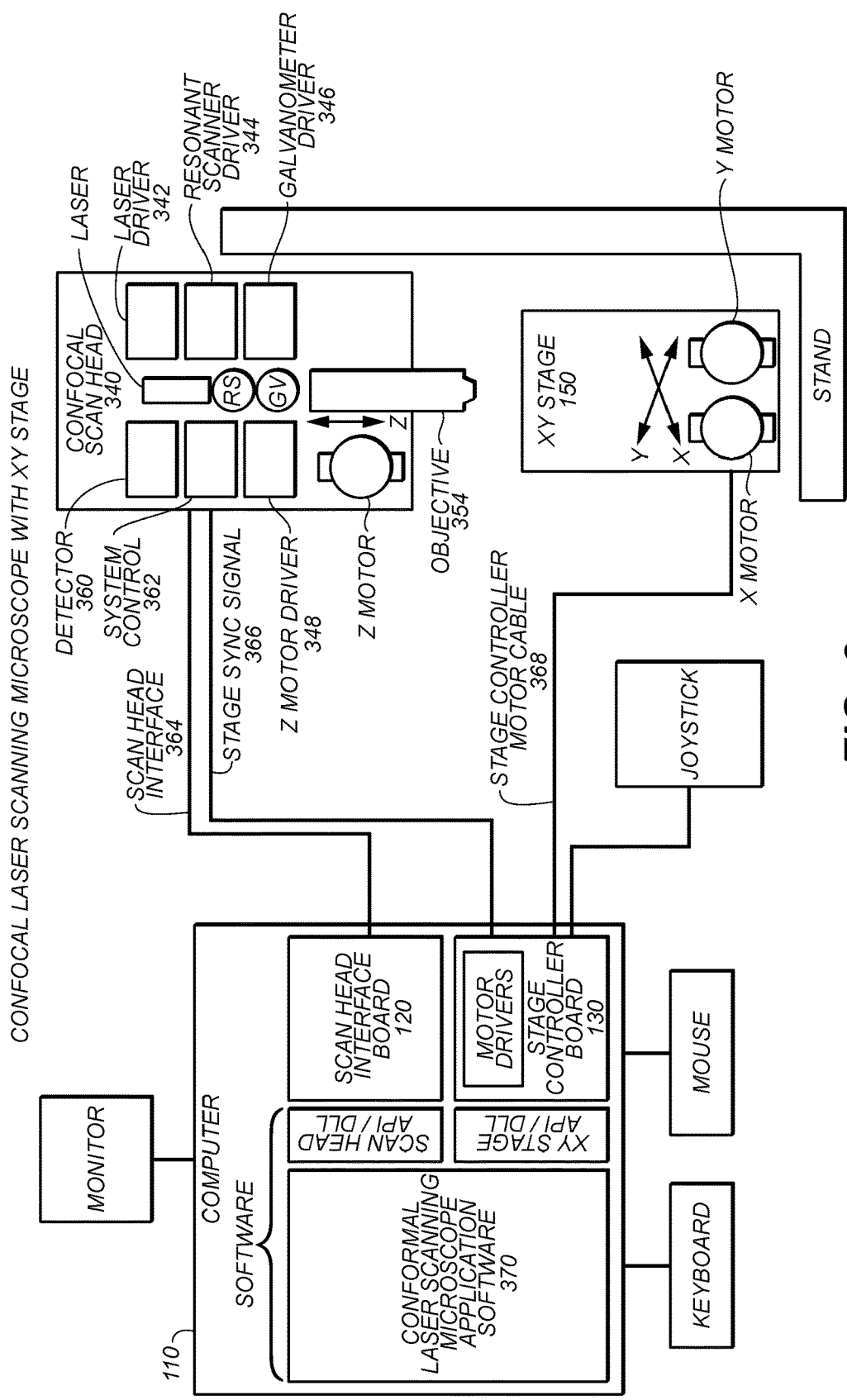
FIG. 3 illustrates a more detailed view of an interface between a confocal laser scanning microscope (CLSM) and a movable stage of FIG. 1, in accordance with the invention.

FIG. 3 illustrates a view of an embodiment of the invention, being a confocal scanning system, that includes a confocal scan head (CSH) 340 which functions as a laser scanning microscope (CLSM) 140 and that includes a movable stage, like that of FIG. 1. As shown in this embodiment of the invention, much of the functionality of the CLSM 140 is packaged into a confocal scan head (CSH) 340. The confocal scan head (CSH) 340 is disposed at a higher elevation relative to the XY stage 150, and functions as a computer separate from the computer 110 of FIG. 1. The system control component 362 of the CSH 340 includes a micro-controller and other hardware and software components.

Unlike the CLSM of FIG. 2, in some modes of operation, referred to herein as strip mapping, movement of the slow scanning mirror 216 within the CSH 340 is eliminated, and instead, substituted for by movement of the XY stage 150 in a direction that is substantially parallel to the Y axis, while the fast scanning mirror 214 of the resonant scanner continues to move in an oscillating fashion that is substantially parallel to the X axis 260. In this mode of operation, movement of the XY stage 150 is synchronized with movement of the fast scanning mirror 214.

In other modes of operation, referred to herein as step mapping or block mosaic scanning, the movement of the XY stage 150 supplements that of the movement of the slow scanning mirror 216 and that of the fast scanning mirror 214.

In this embodiment, the software residing within the CSH 340 includes application software which interfaces with various devices via device drivers. These device drivers include a laser driver 342, which interfaces with a laser component that is also located within the CSH 340. A resonant scanner driver 344 interfaces with a resonant scanner which is located within the CSH 340, and a galvanometer driver 346 interfaces with a galvanometer that is located in the CSH 340, and a Z motor driver 348 that interfaces with a Z motor, which is located inside of the CSH 340. the Z motor is designed to move (raise or lower) the CSH 340 along a direction that is parallel to the Z axis 280.

The CSH 340 also includes a detector module 360, system control hardware 362, and an objective lens 354. Like the detector module of FIG. 2, the detector module 360 of FIG. 3 is designed to input light reflected from each focal plane that is associated with a scanning plane within the specimen 238 (See FIG. 2) that is disposed onto the XY stage 150.

Via the detector module 360, data representing a three dimensional image of at least a portion of the specimen 238 is stored into a memory as digital data. In some embodiments, the data is temporarily stored in memory within the CSH 340 and communicated to another memory that is located outside of the CSH 340, such as stored into memory inside of the computer 110, and communicated via the scan head interface communication channel 364. In other embodiments, the data is communicated directly from the CSH 340 to memory stored inside of the computer 110, via the scan head interface communication channel 364.

Electronics within the system of the invention obtains information regarding the real-time movement of the resonant scanner 220 and in response, the system converts the real-time movement of the resonant scanner 220 into a series of one or more commands, that are communicated from confocal laser scanning microscope (CLSM) application software 370 to the stage controller board 130, via a stage controller motor cable 368.

These commands direct the Stage Controller Board 130 to adjust the velocity of movement of the moving XY stage 150, if necessary, in accordance with the real-time frequency of movement of the resonant scanner 220, which typically varies over time. Such frequency of movement changes can occur in response to changes in a temperature of the resonant scanner 220. In response, the Stage Controller Board 130 communicates and controls the movement of the XY stage 150 via a stage controller motor cable 368.

As shown, the computer 110 includes various user interface components, including a user interface monitor (screen), a keyboard and a mouse (user interface pointing device), and a joystick. A user can employ the computer to position the confocal scan head (CSH) 340 and position the XY stage 150, before or after initiation of scanning by the confocal scanning system. Also, laser poser can be adjusted to adjust image brightness. The stage 150 can be moved below CSH to align specimen into a desired position.

The computer 110 executes confocal laser scanning microscope (CLSM) application software which is designed receive a process inputs from the user interface components, and designed to interface with and interoperate with other components that are in electrical communication with the computer 110, including such as the scan head interface board 120 and the stage controller board 130.

Figure 4:
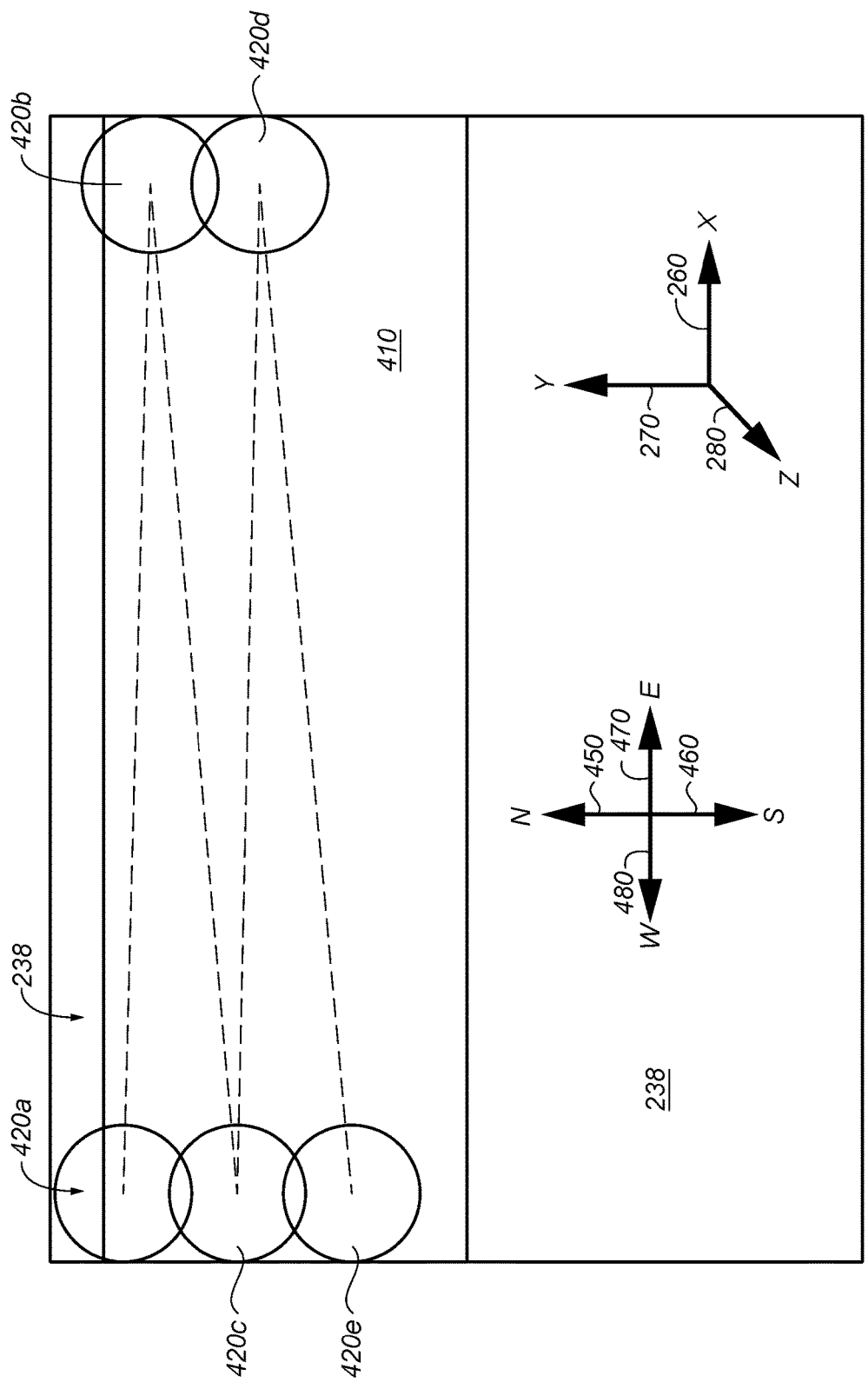
FIG. 4 illustrates a spatial scanning pattern upon a specimen in accordance with the invention.

FIG. 4 illustrates a spatial scanning pattern upon a specimen 238 representing an interoperation between the resonant scanner of the confocal scan head CSH 340 and the moving XY stage 150, in accordance with the invention. As shown, a cross-section of a specimen 238 includes a cross-section of a volume of interest 410, being a layer of tissue within the specimen 238. This layer 410 constitutes a subset of the tissue that is located within the specimen 238. This layer 410 has an upper (most elevated) boundary and a lower (least elevated) boundary that are each planar in shape and parallel to X axis 260 and the Y axis 270. A scanning plane is defined to be a plane in three dimensional space that is oriented parallel to each of the lower and upper boundaries of the layer 410 and that is targeted to reside half way between the upper and lower boundaries of the layer 410. Essentially, the scanning plane is centered with a respect to a center elevation of layer 410 and it is a plane that is located in three dimensional space and within the specimen 238. This scanning plane is a plane along which the optical scanning of the CSH 340 is focused.

A circular shaped portion of a scanning plane that intersects a laser beam that is projected from the CHS 340 is referred to herein as an airy disk (AD) 420. An airy disk 420 is also referred to herein as a laser beam cross-section. This AD 420 represents an area upon which light reflects from the specimen 238 and passes into the light input aperture of the detector module 240. The airy disk 420 moves (oscillates) horizontally (left to right) along the X axis 260, while the XY stage 150 moves the specimen 238 vertically along the Y axis. The CSH 340 (not shown here) is located above (at a higher elevation than) the scanning plane that is located within the specimen 238, and above the specimen itself 238.

Due to the vertical (northerly) movement of the XY stage 150 along the Y axis 270, the horizontal movement of the AD 420 is slanted over time while moving from left to right and from right to left, along the scanning plane and through a cross-section of the specimen 238. As a result, such movement creates a zig-zag like pattern along the scanning plane which passes through a cross-section of the specimen 238.

In accordance with the invention, to scan an entire volume of interest (layer), without missing scanning of a particular location within the volume of interest (layer), movement of the XY stage 150 is controlled to create an intentional overlap between adjacent scan paths along the scanning plane, despite such scan paths moving in a zig-zag like pattern along the scanning plane.

For example, a first segment of a scan path (scan path segment) is defined as residing between airy disk (AD) location at 420a and 420b, and a second scan path segment is defined as being located between AD location 420b and 420c. Notice that the first scan path segment and the second scan path segment overlap each other. The minimum amount of overlap between these two scan path segments is the overlap between the AD at location 420a and 420c. As shown, the overlap between the AD at location 420a and 420c is about 12 percent.

Note that in some embodiments of the invention, optical scanning occurs with movement of the AD 420 in a direction from left to right, but does not occur in with movement of the AD 420 in a direction from right to left. In other embodiments, optical scanning occurs in both directions.

The maximum overlap between scan path segments occurs just prior to when the AD arrives at location 420*b* and just after it departs from location 420*b* and travels towards location 420*c*. In this vicinity of 420*b*, there is nearly a 100% overlap between the arriving and departing AD 420. However, the overlap reduces to about a 12% between when the AD 420 arrives at location 420*c* in relation to where the AD 420 departed location 420*a*.

In some embodiments, each pixel within a scan line is defined to be a center portion of each uniquely located airy disk 420. The span of airy disk itself can cause overlap between adjacent scan lines. Essentially, a center portion of each airy disk can be carved out to define a pixel within that airy disk 420, while a remaining portion of an AD 420 can be discarded.

In other words, a center portion of an airy disk is referred to herein as a pixel. Within these embodiments, such a center portion is defined to be square in shape and is referred to as a square pixel. A required overlap between scan line segments depends upon a relative size between the center portion of the AD and the overall dimensions of the entire AD 420. As a result, some embodiments may require much more than 12% overlap, for example as much as a 50% overlap or more, between adjacent scan path segments to capture and join each and every pixel (center portion) of each AD 420 that resides within the scanning plane of interest.

Note that the XY stage 150 moves in one direction while the resonant scanner mirror oscillates in a direction that is perpendicular to the direction of movement of the XY stage 150. Such movement between the XY stage 150 and resonant scanner takes place over a rectangular area, the span of which defines a frame. A frame is typically a rectangular area having a width that is less than or equal to the horizontal span of the movement of the resonant scanner mirror. The frame having a height that is less than or equal to the span of movement of the XY stage 150.

FIGS. 5A-5B each illustrate a path of stage movement for respectively performing step mapping and strip mapping. FIG. 5A illustrates step mapping, which is also referred to herein as block mosaic mapping or scanning. Referring to FIG. 5A, a frame 510*a*, being a portion of a scanning plane residing along a cross-section of a volume of interest within a specimen 238, is first scanned. The scanning of frame 510*a* initiates with an aim of the CSH 340 directed towards a center of the frame 510*a*, while the resonant scanner fast mirror oscillates between a left hand (western) boundary to a right hand (eastern) boundary of the frame 510*a*, and while the slow mirror moves vertically moves through the frame 510*a* so that the aim of the laser of the CSH 340 continuously covers from the upper (northern) boundary to a lower (southern) boundary of the frame 510*a*, and between the left hand (western) boundary and the right hand (eastern) boundary of the frame 510*a*, and until scanning of the frame 510*a* is complete.

Upon completion of the scanning of frame 510*a*, the XY stage 150 is moved from frame 510*a* to frame 510*b*, so that the scanning of frame 510*b* can be initiated and performed in the same manner as described for frame 510*a*.

The scanning of the (16) frames 510*a* through 510*p* are performed in lexicographic (alphabetic) order over time, meaning in the order of 510*a*, 510*b*, 510*c* . . . 510*p*. The frames 510*a* through frame 510*p* constitute one continuous scanning plane along cross-section of interest within the specimen 238. Tissue within about 1 micron below this scanning plane is referred to as a layer of interest.

It is preferred that there is optical scanning overlap among the (16) frames 510*a*-510*p* that are adjacent to each other. This overlap is employed to join (stich) frames together to form a joined (unified) optical scanning image including all of the (16) frames 510*a*-510*p*). In other embodiments, there may be no overlap between scanned data, such as between the frames, when scanning via step mapping.

In some embodiments, image joining software is implemented using an OpenCV open source library of programming functions. The OpenCV functions are employed to identify like image patterns within adjacently scanned image data, for use as markers for deciding how to align and join together adjacently scanned image data. Such software can join adjacent scanned frames within a same layer, and/or join adjacent frames within separate but adjacent scanned layers.

Such image patterns can be caused by particular cells reflecting light that is directed towards those cells and that within particular wavelength ranges. In some circumstances, injection of various dyes into a layer of the specimen 238 can cause cells within that portion of the specimen 238 to fluoresce, meaning those cells to shine or glow brightly due to fluorescence of the cell that is caused contact between the dye and the cell.

FIG. 5B illustrates strip mapping, which is also referred to herein as strip scanning. Referring to FIG. 5B, a frame 510*q*, having a longer vertical (north/south) dimension relative to its horizontal (west/east) dimension, is also referred to herein as a scanning strip or strip. This strip is 510*q* resides along a scanning plane that is a cross-section of a volume of interest within the specimen 238. The scanning of frame 510*q* initiates at a lower (southern) boundary of frame 510*q*, while the resonant scanner mirror of the SCH 340 oscillates between a left (western) hand boundary and a right (eastern) hand boundary of the frame 510*q*, and while the XY stage 150 moves so that the aim of the confocal scan head (CSH) 340 continuously moves from a lower (southern) boundary of the frame 510*q* to an upper (northern) boundary of the frame 510*q*, in order to complete scanning of the entire frame 510*q*.

The XY stage 150 then moves so that the aim of the CSH 340 is moved outside of any frame (strip) 510*q*-510*t*, and then moving from a right hand (eastern) location to a left hand (western) location, while passing through location 520*c*, which is outside of any frame 510*q*-510*t*, and then moving towards location 520*d*, inside of frame 510*r*, in order to initiate scanning of frame 510*r*. The scanning of frame 510*r* initiates at an upper (northern) boundary, while the resonant scanner mirror oscillates between a left hand (western) boundary and a right hand (eastern) boundary of the frame 510*r*, while the XY stage 150 moves so that the aim of the confocal scan head (CSH) 340 continuously moves between an upper (northern) boundary and a lower (southern) boundary of the frame 510*r*, in order to complete scanning of the frame 510*r*.

The XY stage 150 then moves so that the aim of the CSH 340 is moved outside of any frame 510*r*-510*t*, and then moving from a right hand (eastern) location to a left hand (western) location, while passing through location 520*f*, which is outside of any frame 5104-510*t*), and then moving towards location 520*g*, which is inside of frame 510*s*, in order to initiate scanning of frame 510*s*.

Frame 510*s* is then scanned in the same manner as described herein for frame 510*q*. After scanning frame 510*q*, frame 510*t* is scanned in the same manner as described herein for frame 510*r*. As shown frames 510*q*-510*t*, each have a long rectangular shape, as opposed to having a square shape, like the frames 510*a*-510*p*, of FIG. 5A.

As with adjacent frames, software is employed to join adjacent scanned strips of image data. Such software can join adjacent strips within a same scanned layer, and/or join adjacent strips within separate but adjacent scanned layers.

Figure 6:
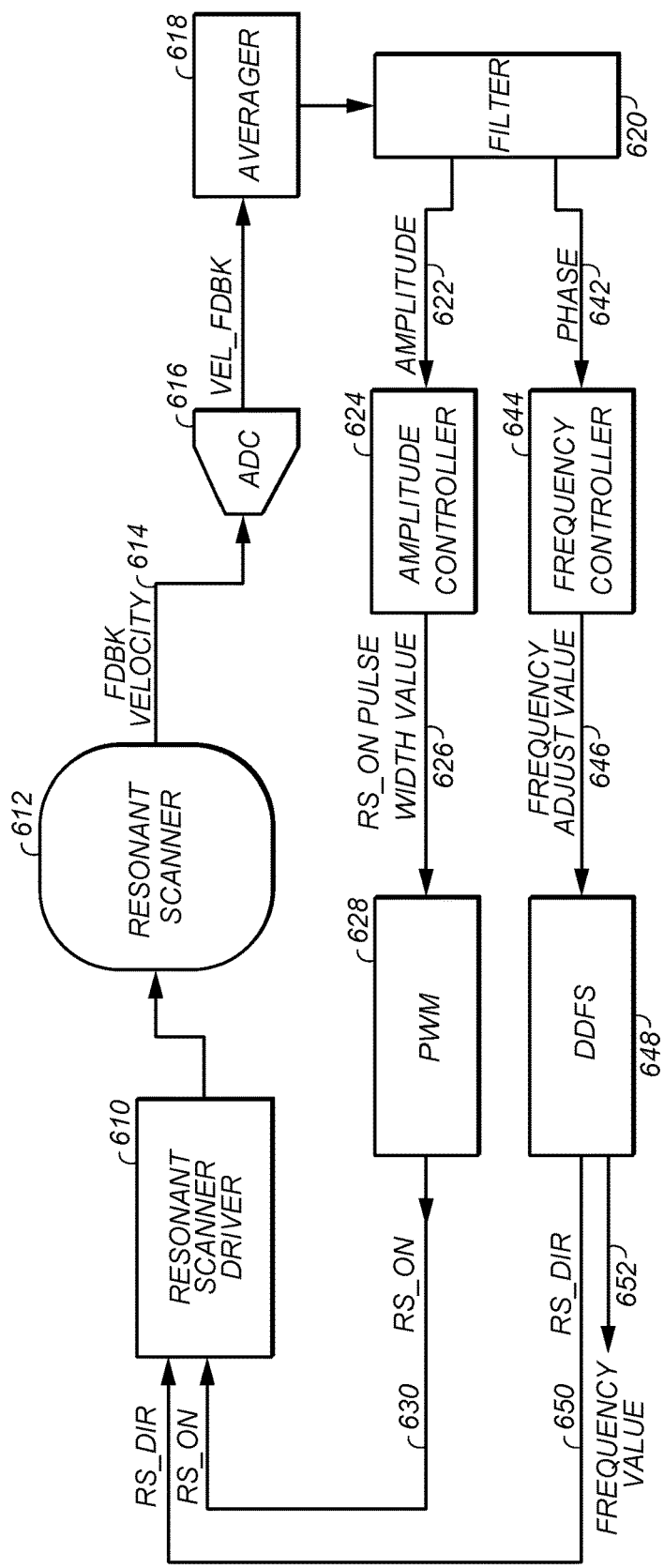
FIG. 6 illustrates a simplified block diagram of an embodiment of a set of electronics that allow interoperation between the confocal scanning head and the XY stage.

FIG. 6 illustrates a simplified block diagram of an embodiment of a set of electronics that allow interoperation between the confocal scanning head 340 and the XY stage 150.

As shown, driver electronics (hardware), a Texas Instrument model DRV8801 610, also referred to as the resonant scanner driver (RSD) component, outputs an electronic signal to a resonant scanner manufactured by Cambridge Technology (Model CRS 8KHz) 612. The resonant scanner outputs an analog electronic signal, referred to herein as a resonating signal (labeled as "Fdbk Velocity" or "Vel fdbk"), is called a feedback velocity signal 614. This feedback velocity signal which represents the movement of the resonant scanner in real-time, meaning that this signal is generated synchronously (near simultaneously) with each physical movement of the resonant scanner within the CSH 340, while it is resonating over time.

A frequency of the resonating signal represents a frequency of resonance of the resonant scanner over time. Because the frequency of a resonating scanner typically changes over time, typically in response to a change in temperature, the frequency of the resonating feedback velocity signal, accordingly changes over time. The amplitude of the resonating feedback velocity signal, at a particular time, represents a location within the scan angle of the resonant scanner where the resonant scanner is directed, at that time. The direction of the resonant scanner oscillates within a range of resonating (oscillating) motion. A maximum amplitude and minimum amplitude of the resonating signal each represent a maximum swing (oscillation) of the laser of the resonant scanner, within its range of resonating (oscillating) motion.

The resonating signal output from the resonant scanner and input into an analog to digital converter (ADC) 616. The ADC 616 outputs a first series of digital values over time. The first series of digital values is input into Average component 618, which outputs a second series of digital values which represent an averaging of segments of the first series of digital values, for the purpose of reducing noise within the signal. In some embodiments, every (4) consecutive values within the first series is averaged into (1) value of the second series of digital values.

The Averager component 618 outputs the second series of digital values into a Filter component 620, which processes those values being input from the Averager 618 to determine an amplitude and phase of the resonating signal over time. The Filter component 620 outputs a first digital signal (amplitude signal), which represents an amplitude of the resonating signal over time, and outputs a second digital signal (phase signal), which represents a phase of the resonating signal over time.

The amplitude signal 622 is input to the Amplitude Controller 624 from the Filter component 620. The amplitude signal 622 is employed as a feedback signal to the Amplitude Controller 624 in order to monitor and adjust the physical range movement of the resonating scanner 612. The Amplitude Controller 624 outputs a pulse width value signal 626 to a Pulse Width Modulator (PWM) component 628 which causes the PWM 628 to output a signal 630 to the resonant scanner driver (RSD) component 610, to adjust, if necessary, the physical range of movement of the resonating scanner 612.

The phase signal 642 is input to the Frequency Controller 644 from the Filter component 620. The phase signal 642 is employed as a feedback signal to the Frequency Controller 644 to monitor and adjust the physical frequency of movement of the resonating scanner 612. The Frequency Controller 644 outputs a frequency adjust value signal 646 to a Direct Digital Frequency Synthesizer (DDFS) 648 which causes the DDFS 648 to output a first signal 650 to the resonant scanner driver (RSD) component 610, to inform the RSD 610 of the actual frequency of physical movement of the resonating scanner 612.

The DDFS 648 outputs a second signal 652 which represents a frequency value which is communicated to the Confocal Laser Scanning Microscope (CLSM) software that executes on the computer 110 (See Page 3). The CLSM software performs an algorithmic computation to convert the frequency value received from the DDFS into a series of one or more commands, that are communicated from the CLSM software to the Stage Controller Board. These commands direct the Stage Controller Board to adjust the velocity of the moving stage, if necessary, in accordance with the current frequency value, and as that current frequency value changes over time.

In some embodiments, when strip mapping, the computation adjusts the velocity of the XY stage 150 at upon completing an optical scan of each strip 510r-510t.

In a circumstance where the frequency of the resonant scanner 612 remains constant over a period of time, then an appropriate velocity of the XY stage 150 will also remain constant over that period of time, in accordance with the constant frequency value for the resonant scanner.

Also, the velocity of the XY stage 150 is determined to provide some overlap (optical scanning overlap) between horizontal and adjacent scan lines obtained by horizontal (east/west) movement of the field of view, caused by the resonance (horizontal oscillation) of the confocal scanning head (CSH) 340 while the XY stage 150 moves in a vertical (north/south) direction relative to the horizontal oscillation of the resonating scanning head.

In some embodiments, the optical scanning overlap, also referred to herein as a target overlap, is typically about 10% of the vertical height of each scan line. For example, if the vertical height of the field of view (FOV), and consequently of each scan line is equal to 1000 microns, then the target overlap would be about 100 microns in size.

For this embodiment, if hypothetically, the stage velocity is perfectly accurate and constant, then there would be a 100 micron overlap of scanned image between each scan line. This overlap enables the image stitching software, to combine two adjacent scan lines into one coherent and accurate image. Small inaccuracies caused by non-optimal (non-perfect) velocity of the stage can be corrected, at the cost of time for computing, by operation of the stitching software, provided that the inaccuracy does not exceed the size of the actual overlap.

Note that in some embodiments, the stage velocity is set to also enable the scanning of square pixels,, which requires the height of each optical scan path to be greater than or equal to a width of each scanned pixel.

In a typical use scenario, the resonant scanner oscillates at a target frequency of 8000 cycles per second. Each pixel has a target width of 0.8 microns. Each horizontal scan line is designed to include 1024 pixels and in combination with the pixel target width, each scan line is approximately (1024 pixels per scan line*0.8 microns per pixel)=819.2 microns in horizontal width, which is also referred to herein as scan line width.

This scan line width equates to 0.8192 millimeters, yielding a scan line of nearly 1 millimeter in horizontal width. In this scenario, a range of direction of the laser beam projected from the confocal scan head CSH 34) would include aiming at the outer boundaries of scan line, and aiming at the entirety of the scan line between its outer boundaries. Such a range of laser beam aiming direction is said to be within the range of the scan angle of the oscillating laser beam, as it is projected from the CSH 340.

In order to enable scanning of square pixels, the XY stage 150 should move at a target stage velocity of (8000 cycles/sec)*(0.8 microns height per pixel)=6400 microns per second to accommodate a pixel height equal to 0.8 microns.

However, should the resonant frequency of the resonant scanner vary by a maximum of plus or minus 2 cycles per second, this could alter the target XY stage velocity to a range between 6398.4 microns per second and 6401.4 microns per second.

For example, in response to the varying resonant frequency, the target stage speed would be (7998 cycles per second*0.8 microns per pixel)=6398.4 microns per second when the resonant scanner frequency drifts down to 7998 cycles per second. Alternatively, the target XY stage speed would be (8002 cycles per second*0.8 microns per pixel)=6401.4 microns per second when the resonant scanner frequency drifts up to 8002 cycles per second. The target stage velocity its controlled to match the resonant scanner frequency near instantaneously and in real time.

In another use scenario, reduction of optical noise within the optical scanning of the specimen can be reduced by reducing the target XY stage speed by one half. In this scenario, optical scanning of two adjacent scan lines are averaged to reduce optical noise. This technique is said to employ over sampling. This technique can be used to improve upon (increase brightness of) what would otherwise be scanned images that appear dim as seen from a human eye.

In other use scenarios, different operating parameters, such as a different target resonant scanner frequency, different pixel size and pixel shape, and different target XY stage velocity can be employed for various purposes. This written description uses example embodiments to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Parts List 110 computer
120 CLSM interface board
130 stage controller board
140 CLSM
150 XY stage
210 laser module
212 beam splitter
214 fast scanning mirror
216 slow scanning mirror
218 galvanometer
220 resonant scanner
230 telescope
232 wave plate
234 objective lens
236 window
238 specimen
240 detector module
242 detector module input lens
260 X axis
270 Y axis
280 Z axis
340 confocal scan head
342 laser driver
344 resonant scanner driver
346 galvanometer driver
348 Z motor driver
354 objective lens
360 detector
362 system control
364 scan head interface
366 stage sync signal
368 stage controller motor cable
410 layer volume of interest
420 airy disk
420a- 420e locations of airy disk
450 north direction
460 south direction
470 east direction
480 west direction
510 frame
510a- 510p locations of different frames
610 Texas Instruments Drive DRV8801
612 resonant scanner Cambridge Technology CRS 8KHz
614 feedback velocity
616 analog to digital converter
618 averager
620 filter
622 amplitude signal
624 amplitude controller
626 pulse width value
628 pulse width modulator (PWM)
630 PWM output signal
642 phase signal
644 frequency controller
646 frequency adjust value
648 direct digital frequency synthesizer (DDFS)
650 DDFS output signal
652 frequency value

The invention claimed is:
1. A system for scanning tissue, comprising:
a resonant scanner that is configured for optical scanning of a specimen, and wherein a direction of said optical scanning is performed within an oscillating pattern that cycles in between two extreme locations that define a line that is substantially parallel to a first axis;
a stage that is configured to move in at least one direction, said direction being substantially parallel to a second axis that is perpendicular to said first axis, and wherein said stage is configured to move at a velocity in accordance with control signals that are received by said stage;
a set of electronics that is configured to obtain a frequency of resonance over time of said resonant scanner, and wherein said set of electronics controls a velocity of movement of said stage over time, via communication of said control signals to said stage in response to said frequency of resonance over time.

2. The system of claim 1 wherein the stage is controlled to perform strip mapping.

3. The system of claim 1 wherein the stage is controlled to perform step mapping.

4. The system of claim 1 wherein the set of electronics includes a direct digital frequency synthesizer.

5. The system of claim 1 wherein the stage velocity is controlled to enable square pixels to be scanned.

6. The system of claim 2 wherein adjacent strips within one layer are joined together to join scan data between multiple strips within said layer of said specimen.

7. The system of claim 6 wherein adjacent layers within a specimen are joined together to obtain joined scan data across multiple layers within one specimen.

8. An apparatus for scanning tissue, comprising:
a resonant scanner that is configured for optical scanning of a specimen, and wherein a direction of said optical scanning is performed within an oscillating pattern that cycles in between two extreme locations that define a line that is substantially parallel to a first axis;
a stage that is configured to move in at least one direction, said direction being parallel to a second axis that is perpendicular to said first axis, and wherein said stage is configured to move at a velocity in accordance with control signals that are received by said stage;
a set of electronics that is configured to obtain a frequency of resonance over time of said resonant scanner, and wherein said set of electronics controls a velocity of movement of said stage overtime, via communication of said control signals to said stage in response to said frequency of resonance over time.

9. The apparatus of claim 8 wherein the stage is controlled to perform strip mapping.

10. The apparatus of claim 8 wherein the stage is controlled to perform step mapping.

11. The apparatus of claim 8 wherein the set of electronics includes a direct digital frequency synthesizer.

12. The apparatus of claim 8 wherein the stage velocity is controlled to enable square pixels to be scanned.

13. The apparatus of claim 9 wherein adjacent strips within one layer are joined together to join scan data between multiple strips within said layer of said specimen.

14. The apparatus of claim 13 wherein adjacent layers within a specimen are joined together to obtain joined scan data across multiple layers within one specimen.

15. A method for scanning tissue, comprising the steps of:
providing a resonant scanner that is configured for optical scanning of a specimen, and wherein a direction of said optical scanning is performed within an oscillating pattern that cycles in between two extreme locations that define a line that is substantially parallel to a first axis;
providing a stage that is configured to move in at least one direction, said direction being parallel to a second axis that is perpendicular to said first axis, and wherein said stage is configured to move at a velocity in accordance with control signals that are received by said stage;
providing a set of electronics that is configured to obtain a frequency of resonance over time of said resonant scanner, and wherein said set of electronics controls a velocity of movement of said stage over time, via communication of said control signals to said stage in response to said frequency of resonance over time.

16. The method of claim 15 wherein the stage is controlled to perform strip mapping.

17. The method of claim 15 wherein the stage is controlled to perform step mapping.

18. The method of claim 15 wherein the set of electronics includes a direct digital frequency synthesizer.

19. The method of claim 15 wherein the stage velocity is controlled to enable square pixels to be scanned.

20. The method of claim 16 wherein adjacent strips within one layer are joined together to join scan data between multiple strips within said layer of said specimen.

21. The method of claim 20 wherein adjacent layers within a specimen are joined together to obtain joined scan data across multiple layers within one specimen.

* * * * *